US006537566B1

United States Patent
Copland et al.

(10) Patent No.: US 6,537,566 B1
(45) Date of Patent: Mar. 25, 2003

(54) COMPOSITIONS AND METHODS FOR THE NON-INVASIVE TREATMENT OF UTERINE FIBROID CELLS

(76) Inventors: John Alton Copland, 747 Cambridge, #71, Houston, TX (US) 77054; Steven L. Young, 4817 Woodrow Ave., Galveston, TX (US) 77551

( * ) Notice: Subject to any disclaimer, the term of this patent is extended or adjusted under 35 U.S.C. 154(b) by 0 days.

(21) Appl. No.: 09/520,592

(22) Filed: Mar. 8, 2000

Related U.S. Application Data

(60) Provisional application No. 60/123,987, filed on Mar. 11, 1999.

(51) Int. Cl.$^7$ ................................................. A61F 13/00
(52) U.S. Cl. ........................ 424/422; 424/430; 424/431; 424/432; 424/433; 424/434; 514/944; 514/945; 514/953; 514/967; 530/388.21; 436/8
(58) Field of Search ................................ 424/422, 430, 424/431, 432, 433, 434; 436/8; 530/388.21; 514/944, 945, 947, 953, 967

(56) References Cited

U.S. PATENT DOCUMENTS

| 4,963,525 A | 10/1990 | Alexander ..................... 514/11 |
| 5,788,980 A | 8/1998 | Nabchi .......................... 424/430 |
| 5,816,248 A | 10/1998 | Anderson ..................... 128/830 |
| 5,972,372 A | 10/1999 | Saleh ........................... 424/432 |
| 5,981,719 A | 11/1999 | Woiszwillo ................... 530/410 |
| 5,993,856 A | 11/1999 | Ragavan ...................... 424/489 |

OTHER PUBLICATIONS

Fruscella et al. Vitamin E in the treatment of pregnancy complicated by uterine myoma. Minerva Ginecol. 1997, 49(4):175–179.*

Sell et al. Molecular analysis of chromosome 7q21.3 in uterine leiomyoma: analysis using markers with linkage to insulin resistance. Cancer Genet. cytogenet. 1998 Jan.: 15; 100(2):165–168.*

Hehenberger et al. high–glucose induced growth factor resistance in human fibroblasts can be reversed by antioxidants and protein kinase C–inhibitors. Cell Biochem. Funct. 1997. Sep.; 15(3); 197–201.*

Howe, et. al., Rodent Model of Reproductive Tract Leiomyomata: Characterization and Use in Preclinical Therapeutic Studies, Prog. Clin. Biol. Res. 396 (1997).

(List continued on next page.)

Primary Examiner—Thurman K. Page
Assistant Examiner—Lakshmi Channavajjala
(74) Attorney, Agent, or Firm—Shernan D. Pernia

(57) ABSTRACT

The proliferation of uterine fibroid leiomyoma cells is inhibited by certain Fibroid Cell Growth Inhibitor (FGI) agents. The pharmacological doses of these FGI agents in the milieu of uterine fibroid cells can be made high enough to not only inhibit proliferation, but to also causes cell death. Non-invasive or minimally invasive, non-systemic delivery methods are used to deliver the FGI agent to the milieu of the target fibroid leiomyoma cell population, thereby avoiding the disadvantages and side effects of surgical and systemic hormonal therapy interventions in the treatment of uterine fibroids. The FGI agents are substrates that are normally present or are well tolerated in the human body. The efficacy of the FGI agents appears to be related to their ability to moderate the Protein Kinase C and Mitogen Activated Protein Kinase pathways. Specific FGI agents shown to be useful to inhibit growth or proliferation of uterine fibroid cells include: α-tocopherol, α-tocopherol succinate, and troglitazone. Delivery of the FGI agents to the milieu of the target uterine fibroid cells may be accomplished by intra-vaginal and in situ injection techniques already known in the art.

16 Claims, 7 Drawing Sheets

OTHER PUBLICATIONS

Howe, et. al., Estrogen Stimulation and Tamoxifen Inhibition of Leiomyoma Cell Growth in Vitro and in Vivo Endocrinology, 136:4996–5003 (1995).

Uterine Leiomyomata, ACOG Technical Bulletin, No. 192 (May 1994).

Boscoboinik, et.at., Inhibition of Cell Proliferation by a–Tocopheral, Role of Protein Kinase C, J. Biol. Chem. 266(10): 6188–6194 (1991).

Caponigro, et al., Protein Kinase C: a worthwhile target for anticancer drugs?, Anticancer Drugs 8(1): 26–33 (1997).

Bulletti, et.a;., Human Reproduction, v12(5):1073–1079 (1997).

Young and Copland, Vitamin E is a potent Inhibitor of leiomyoma cell growth, J. Soc. Gynecolgical Investigation, 6(1): 720 (1999).

Palan et.al., Lipid–Soluble Antioxidants: b–Carotine and a–Tocopheral Levels in Breast and Gynecological Cancers, Gynocological Oncology, 55:72–77 (1994).

Beck, et.al., Long–acting injectable microsphere formlation for parenteral administration of levonorgestrel, Advances in Contraception 1:119–129 (1985).

Bhasin, et al., A Biodegradable Testosterone Microcapsule Formulation Provides Uniform Eugonadal Levels of Testosterone for 10 11 Week in Hypogonadal Men, J. Clinical Endocrinology and Metabolism, 74 (1): 75–83 (1992).

Burns, et.al., Nafarelin controlled release injectable: theoretical clinical plasma profiles from multiple dosing and from mixtures of microspheres containing 2 per cent 4 per cent and 7 per cent Nafarelin, J. Microencapsulation 7(3):397–413 (1990).

Ultra–Long Duration Local Anesthesia Produced by Injection of Lecithin–Coated Tetracaine Microcrystals, J. Clin. Pharmacol. 34:699–702 (1994).

Luteal support after in–vitro fertilization: Crinone 8%, a sustained release vaginal progesterone gel, versus Utrogestan, an oral micronized progesterone, European Soc. Human Reproduction and Technology—1996 09–; 11(10):2085–2089.

* cited by examiner

COMPOSITIONS AND METHODS FOR THE NON-INVASIVE TREATMENT OF UTERINE FIBROID CELLS

The present application claims the benefit of prior filed U.S. Provisional Application, Ser. No. 60/123,987, filed Mar. 11, 1999, to which the present application is a regular U.S. national application, the content of which is incorporated herein by reference, to the same extent as had it been recited herein in its entirety.

FIELD OF THE INVENTION

The present invention is in the field of bio-effecting compositions and methods. More specifically, the present invention relates to compositions and methods of using the compositions to inhibit the growth of uterine fibroid cells.

BACKGROUND OF THE INVENTION

Uterine Fibroids

Uterine fibroids (leiomyomata) are "benign" tumors of the uterus, which occur in about 20 percent of women of reproductive age. Uterine fibroids are one of the most common tumors. Complications arising from uterine fibroids account for about 30% of all hysterectomies performed in the U.S., with a resulting direct cost of inpatient care of about $1 billion per year. Despite this enormous impact on women's health, the factors causing formation and growth of these benign tumors remain largely enigmatic.

A uterine fibroid (leiomyomata) consists of a mass or population of smooth muscle cells and connective tissue that grows, usually slowly, within the uterine wall. Epidemiologic studies demonstrate that fibroids initially form after menarche. It is suspected that fibroid growth is due to a monoclonal, deregulated proliferation of uterine smooth muscle myometrial cells. The primary tumor cell type resulting from the growth of the fibroid are derived from myometrial cells and are referred to herein as leiomyoma cells. Uterine fibroid leiomyoma cells tend to proliferate during pregnancy and regress in menopause. Studies have clearly implicated gonadal steroids (estrogen and progesterone) as a likely factor in formation and growth of these benign tumors. This has motivated the search for therapies aiming at suppressing endogenous gonadal steroid production.

Treatment of Fibroids

Chemical intervention has focused on a class of compounds which previously had shown efficacy at reducing the circulating concentration of steroids and reducing myoma volume. These compounds are the Gonadotropin Releasing Hormone (GnRH) agonists: GnRHa. Other factors which have been implicated in stimulation of fibroid growth include Insulin-like Growth Factor-1 (IGF-1), Insulin, Growth Hormone, Epidermal Growth Factor (EGF), Transforming Growth Factor (TGF), and Basic Fibroblast Growth Factor (bFGF). However, chronic therapy with GnRHa has not gained widespread acceptance for the following reasons:

1. GnRHa is an expensive medication which generally must be given by injection.
2. The maximal effect of GnRH agonist is seen at 12 weeks, after which no further volume reduction is seen.
3. Although the median uterine volume reduction seen is about 50%, individual fibroids can vary greatly in response.
4. Rapid increases in both uterine and fibroid size are seen after discontinuation of therapy.
5. Chronic hypoestrogenemia, resulting from GnRH agonist use, causes osteoporosis, increased risk of heart disease, hot flashes, vaginal dryness, and mood swings. Some of these symptoms can be ameliorated by addition of daily low dose estrogen and progestin, which may compromise efficacy in some individuals and increases cost and complexity of therapy.
6. Present chemical interventions are administered systemically.

Surgical intervention in the treatment of fibroids can range from myomectomy to total hysterectomy, where the fallopian tubes and uterus are completely removed. As with all such surgeries, these treatments are extremely invasive. In addition to the risks generally associated with surgical interventions, infertility can result. However, in spite of the disadvantages of surgical intervention, the frequency of its use in the treatment of fibroids is indicative of the limitations of chemical intervention in relieving or controlling the condition in women.

Therefore, it would be beneficial to have a therapeutic option for the treatment of fibroids that is not invasive, as is surgery, and does not have the side effects of systemically administered hormonal therapies.

SUMMARY OF THE INVENTION

The present invention is the combination of compositions and methods for treating uterine fibroids by inhibiting the growth of uterine fibroid leiomyoma cells. The present invention uses non-hormonal compositions, and non-invasive or minimally-invasive delivery methods to non-systemically administer the compositions. The inhibition of cell growth involves the blocking of cell division and/or DNA replication in the target cells in order to retard the rate of increase of the cell population, to stabilize the cell population, or to reduce the number of cells in the cell population.

Myometrial cells are smooth muscle cells of the uterus. Leiomyoma cells are derived from myometrial cells, and are the tumor cell type which substantially comprise the population of cells of a uterine fibroid. A cell population, for the purpose of this invention includes a uterine fibroid or a collection or concentration of leiomyoma cells, which cells are the target of the present invention. The compositions of the present invention are formulations of an active agent, plus any carrier and formulary materials to which a subject's tissue is initially exposed. An agent is a substrate that is a fibroid cell growth inhibitor. A carrier is a substance that facilitates the agent's interaction with a transport or communication mechanism that moves substrates into the milieu of the fibroid cells. A dose is an amount of composition containing a sufficient concentration of agent to inhibit or reduce proliferation after transport into the milieu of the target cells. A communication or transport means is a mechanism by which the agent is moved from the point of the subject's exposure to the composition into the milieu of the target cells. A vehicle is the physical packaging of the composition as administered to a subject to be treated. A delivery or release device is a "hardware" type of delivery vehicle.

The delivery vehicle of the present invention is any means for containing a composition comprising an agent useful for inhibiting uterine fibroid cell growth, and releasing it to enter into a communication or transport means. A transport means preferably is a natural mechanism for communicating agent substrate from the delivery vehicle into the milieu of the target cell population. Such communication means includes chemical means such as diffusion, gradient transport, etc., and biological means such as closed or preferential type circulatory means (e.g., the uterine first pass effect).

Generally, the methods of treatment of the present invention comprises: giving a dose of composition that incorporates a fibroid cell growth inhibitor (FGI) agent to a subject to be treated for uterine fibroids. The dose is delivered non-systemically by placing it as proximate as possible to the uterine fibroid cells to be inhibited.

The FGI agent in the composition of the dose is a substrate that is normally present and physiologically well tolerated in humans or an analog or derivative of such a substrate. The dose of composition contains a sufficient amount of the FGI agent such that, upon transport of the agent into the milieu of the uterine fibroid cells, the delivered amount is effective to inhibit the growth of said cells. After delivery of the dose of the composition proximate the fibroid cells, the fibroid cells are exposed to the FGI to the agent to inhibit their growth. Examples of fibroid cell growth inhibitor (FGI) agents are substrates that are a protein kinase C pathway inhibiting compound; a direct protein kinase C inhibitor; an α-tocopherol, its derivatives or analogue; and a MAP kinase inhibitor. Certain thiazolidinediones have been demonstrated to effect PKC mediated pathway, in view of which makes them identified potential FGI agents. The determination of any specific identified potential FGI agent as an actual FGI agent may be accomplished according to Example 1, below.

Identified FGI agents potentially useful in the practice of the present invention include: α- and β-tocopherols, α-tocopherol succinates, thiazolidinediones (e.g., troglitazone), bisindolemalemides, (e.g., GF109203x), U73122, and PD98059. Additionally, appropriate FGI agents include signaling molecules that effect the Protein Kinase C and MAP kinase pathways.

The composition contains an amount of the FGI agent sufficient to inhibit the growth of uterine fibroid cells upon delivery into the milieu of the fibroid. The composition may be pure FGI agent or may be a mixture of the active agent in a carrier media. The composition may be packaged in a vehicle to facilitate its delivery to a subject. Delivery vehicles adaptable by one of ordinary skill in the art for use with the present invention include: suppositories, tampons, creams, pessaries, micro-capsules and intra-vaginal drug dispensing or releasing devices as are known in the art.

The method of the present invention may be practiced in at least two primary ways, intra-vaginally and in situ. Intra-vaginal delivery is a non-invasive method of administering FGI agents. It is non-invasive in that it does not require the artificial penetration of the epithelium (skin) to accomplish delivery of the substrate to the target site. In situ delivery is a minimally invasive method in that it may be accomplished with only the puncture or the making of a small incision in the skin.

In the intra-vaginal method, the composition is delivered by inserting the composition or the vehicle carrying the composition into the vagina of a woman to be treated for uterine fibroids, proximate the uterus, and in communication with the tissue of the vaginal wall. In this method, the FGI agent is released from the composition into communication with the tissue of the vaginal wall. The release of the FGI agent from the composition depends on the nature of the composition and the vehicle, if any, used to deliver the composition. After the FGI agent is released from the composition and contacts and enters the tissue of the vaginal wall, it is transported from the vaginal tissue to the tissue of the uterus via a pathway identified as the "first uterine pass mechanism." Bulletti et al., Human Reproduction, v12(5) :1073–1079 (1997). This method may also be practiced by containing the composition in a vaginal release device, and inserting the device into the vagina of a subject to be treated for uterine fibroids proximate the uterus, as described above. The composition containing the FGI agent is released from the device according to the design of the device and into communication with the tissue of the vaginal wall. As further described above, the FGI agent is transported from the vaginal tissue to the tissue of the uterus and hence the milieu of a uterine fibroid via the "first uterine pass mechanism."

Vehicles appropriate for carrying the composition to accomplish intra-vaginal delivery include: creams, gels, suppositories, pessaries, and intra-vaginal release devices. Such vehicles as may be inserted into the uterus directly would also be appropriate for use with the present invention.

In the in situ method, the composition is delivered by injecting it directly into the uterus of a woman to be treated, preferable proximate a fibroid to be treated. When it is desirable to deliver a large dose of FGI agent to accomplish a relatively immediate, high level effect, the composition may be injected by syringe directly into a fibroid cell mass. The location of the intended injection site may be determined by palpating the fibroid (if large enough) or by an imaging means such as sonography, laparoscopy, x-ray, MRI or the like. If desired, a more constant dosing with an FGI agent may be accomplished using in situ injection by containing or formulating the composition in a time release vehicle, such as a micro-capsule, and injecting the micro-capsules by syringe into the uterine tissue generally, or directly into the fibroid to be treated. The micro-capsule may be injected generally into the uterine tissue, but preferable would be injected proximate or directly into the uterine fibroid to be treated, to permit the controlled time release of the FGI agent directly into the milieu of the fibroid. In situ or intrauterine delivery of a FGI agent (such as by the injection of micro-capsules) into or near the leiomyoma can be accomplished under non-invasive guidance of an imaging means or by palpation, as noted above.

Basically, the system of the present invention, for inhibiting the growth or proliferation of uterine fibroid leiomyoma cells, comprises a population of uterine fibroid cells in which the growth of such cells is to be inhibited; a fibroid cell growth inhibitor agent effective to inhibit the growth of uterine fibroid cells; a vehicle for containing and delivering the agent in a controlled manner into communication with the uterine fibroid cells so that the agent can inhibit the growth of the uterine fibroid cells.

DETAILED DESCRIPTION OF THE INVENTION

Figure 1B:
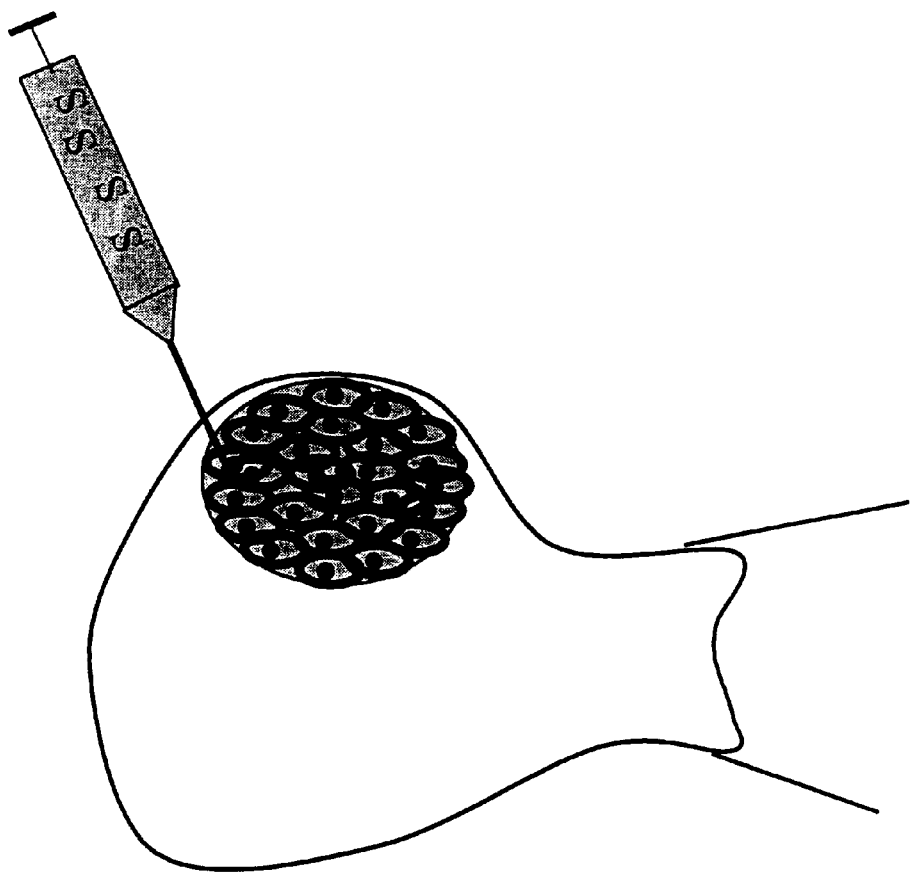
FIGS. 1A & 1B provide an overview representation of the present invention as practiced using (A) an intra-vaginal delivery method, and (B) an in situ delivery method.
Figure 1A:
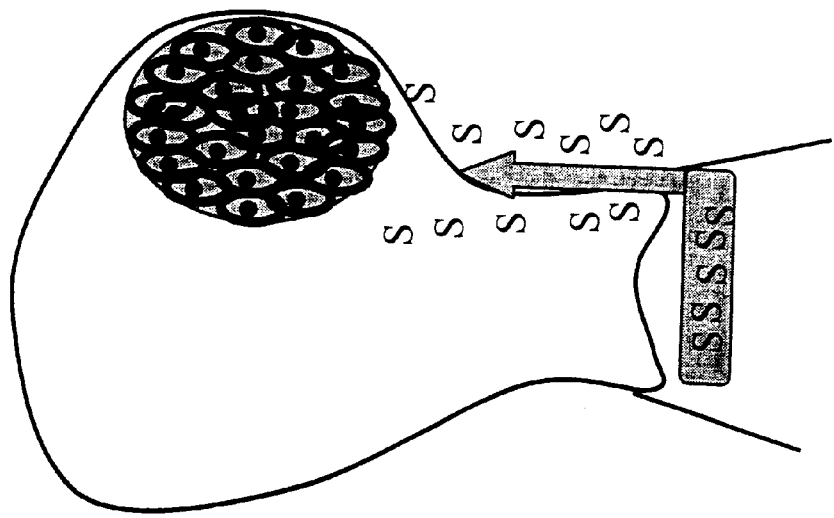

As shown in FIGS. 1A & 1B, the present invention comprises a population of uterine fibroid cells, a means for communicating an effective amount of a Fibroid Growth Inhibitor (FGI) agent into the milieu of the uterine fibroid cells in the population to inhibit the growth and proliferation of the fibroid cells. FIG. 1A is a representation of the present invention practiced using an intra-vaginal delivery method where the, and FIG. 1B, an in situ delivery method.

Figure 2:
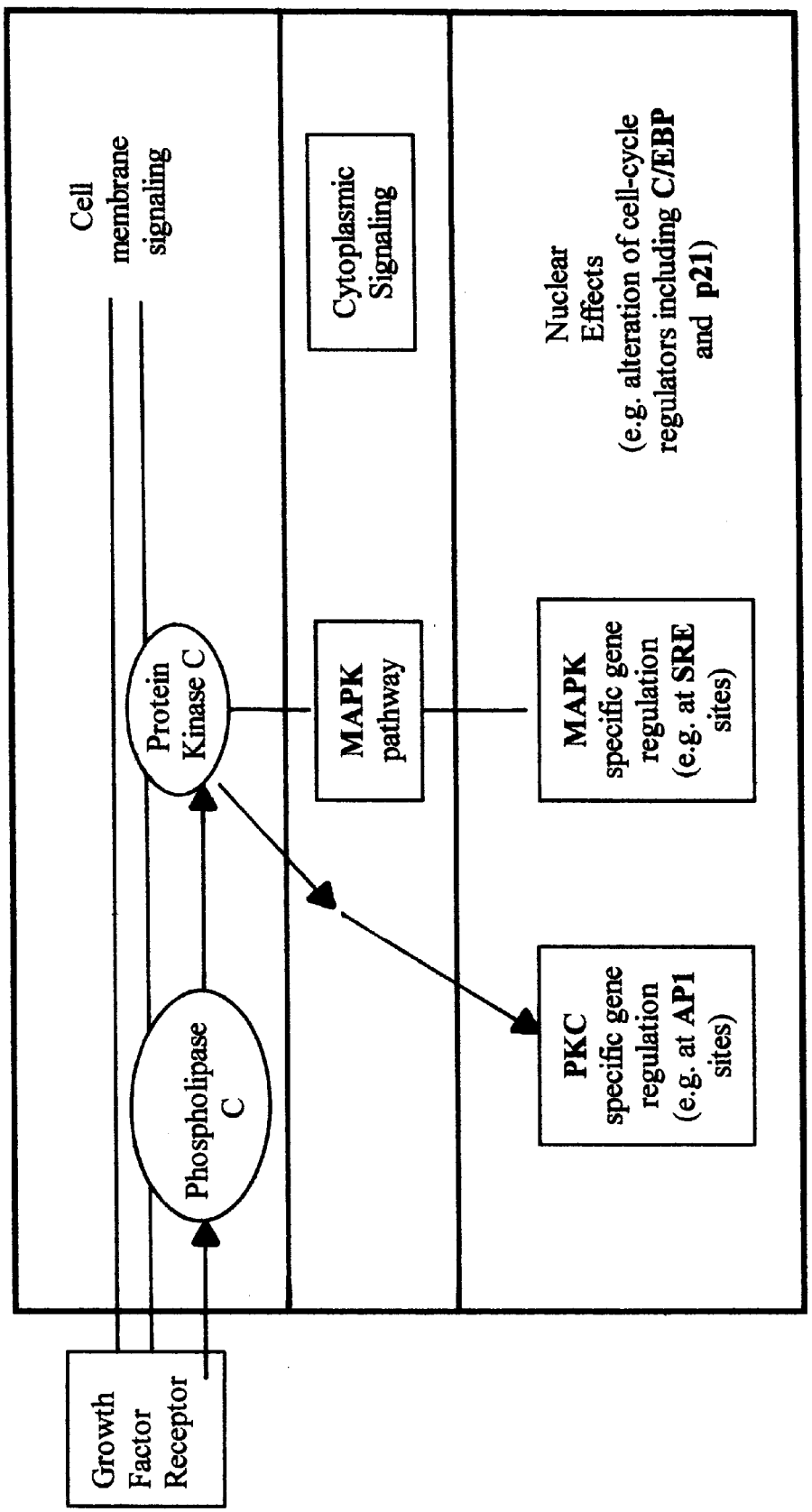
FIG. 2 is a schematic representation of the Protein Kinase C (PKC) pathway and Mitogen Activated Protein (MAP) kinase pathway, showing the relationship between the two pathways.

Generally, the present invention is a non-systemic, non-invasive or minimally invasive method of treating uterine fibroids by inhibiting the growth of uterine fibroid cells using non-hormonal substrates. The FGI agents of the present invention are preferably substrates (or analogue or derivatives of substrates) that are normally present and physiologically well tolerated in humans. The growth of uterine fibroids appears to be mediated by various growth factors which use a number of different signaling pathways to promote growth and proliferation of uterine fibroid leiomyoma cells. We have identified the Protein Kinase C (PKC) pathway as central to uterine fibroid leiomyoma cell growth. Young & Copland, *Vitamin E is a potential inhibitor of leiomyoma cell growth,* J. Soc.Gynecological Investigation, 6(1):720 (1999). Therefore, substrates that inhibit the PKC pathway were identified as potential fibroid cell growth inhibiting agents. Further, the protein kinase C substrate itself appears to act, at least in part, through activation of the Mitogen Activated Protein (MAP) kinase pathway. In view of this, substrates which inhibit the MAP kinase pathway also were identified as potential FGI agents. Such a substrate is PD98059, which inhibits a signaling molecule that activates MAP kinase. FIG. 2 is a graphically representation of the relationship between the PKC and MAP kinase pathways. Effecting the PKC and/or MAP kinase pathways appears to alter the activity of a number of cell cycle regulators, to inhibit cell proliferation and induce apoptosis—programed cell death. Inhibition of the Protein Kinase C pathway can also be accomplished by substrates which activate protein phosphatase A2, which dephosphorylates protein kinase C.

Generally, the system of the present invention for inhibiting the growth or proliferation of uterine fibroid leiomyoma cells comprises a cell population of uterine fibroid cells in which growth or proliferation is to be inhibited, an FGI agent effective to inhibit the growth of leiomyoma cells, a vehicle for containing and delivering the agent to a communication or transport means for transporting the FGI agent into the milieu of the cell population so that the FGI agent can inhibit the growth of the uterine fibroid leiomyoma cells.

As shown in FIG. 3, a number of FGI agents have been experimentally determined. These include in order of decreasing efficacy under the conditions shown in FIG. 3: α-tocopherol succinate>troglitazone>rosiglitazone=pioglitazone>α-tocopherol>β-tocopherol. The method of Example 1, as well as others, may be used by the ordinary skilled artisan to determine other FGI agents.

EXAMPLE 1

DNA Content of Leiomyoma Cells Treated with Different Fibroid Cell Growth Inhibitor (FGI) Agents A DNA assay was used for determining the effect of potential FGI agents on the growth of uterine fibroid leiomyoma cells. The assay determined the effect of various concentrations of an individual FGI agent on the accumulation of DNA in an actively growing population of uterine fibroid leiomyoma cells. The accumulation of DNA in treated cell populations relative to untreated controls was an indication the efficacy of the FGI agent for inhibiting fibroid cell proliferation.

Figure 3A:
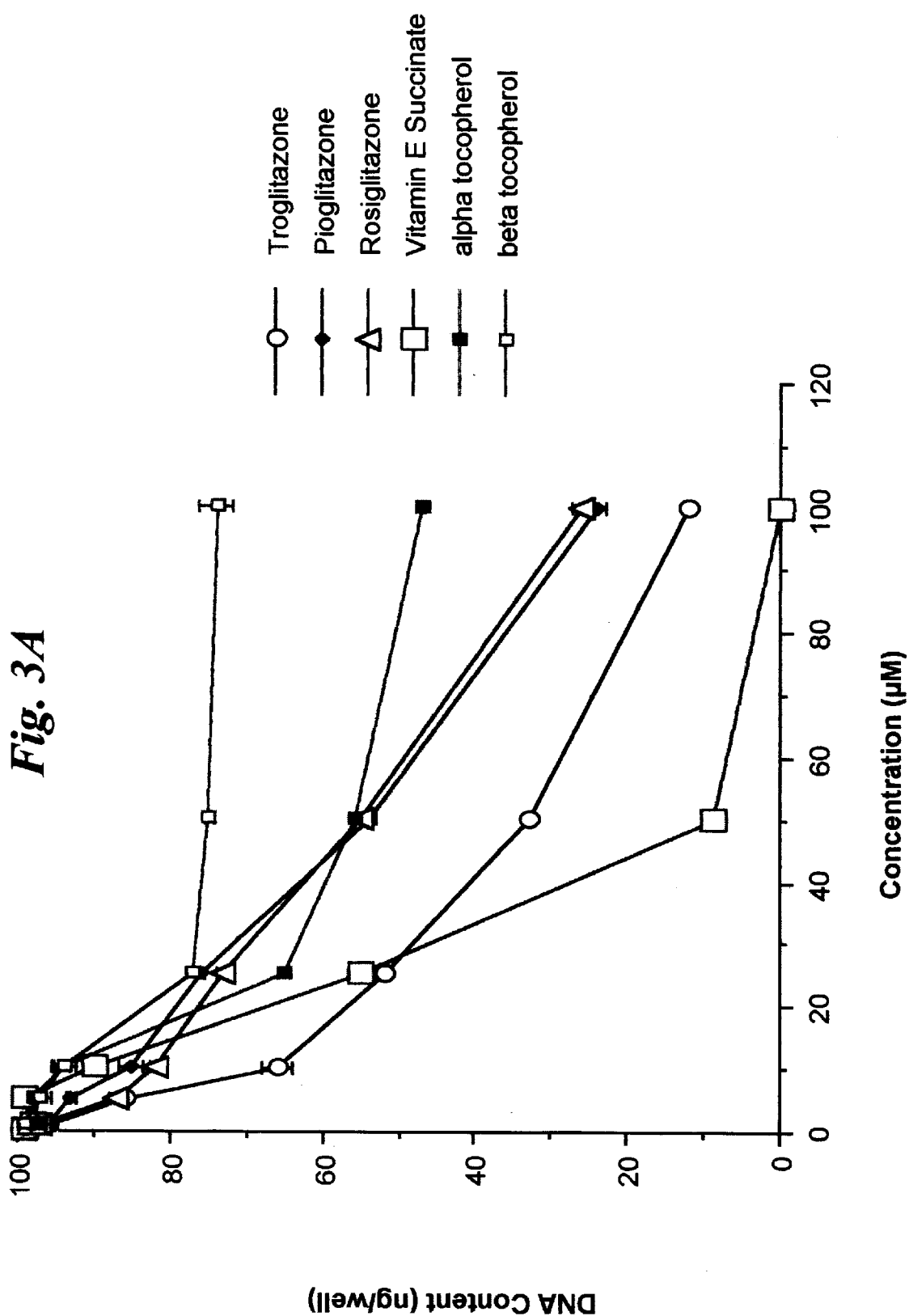
FIGS. 3A is a graph of the dose dependent inhibition of the growth of leiomyoma cells treated with different Fibroid Cell Growth Inhibitor (FGI) agents in the experiment of Example 1.

Method: Fibroid tissue was obtained from patients undergoing hysterectomy for symptomatic leiomyomata, and leiomyoma cells were isolated from the tissue using standard techniques. Leiomyoma cells in 5% fetal calf serum were plated at 22,000 cells/well in 12-well plate. Cells were allowed to acclimate and grow for 24 hours before the start of the experiment. At time=0, the DNA content of the wells was determined (32+/−0.6 ng/well), and the cells were treated with different concentrations of the FGI agents as shown in FIG. 3A in 5% fetal calf serum. Controls received fetal calf serum alone. After treatment at time=4 days, the DNA content of each well was determined using standard methods. All points were determined in triplicate and are the mean +/− standard error.

Results: See Table 1. The time=0 starting concentration of DNA was 32 +/−0.6 ng/well. The DNA concentration of controls at time=4 days was 96+/−1.0 ng/well (the "0" concentration in FIG. 3A). This difference between controls at time=0 and at time=4 days indicated that untreated cell populations doubled 1.69 times in the 4 days of the experiment.

TABLE 1

Experimental Results, Example 1:
Addition of Identified FGI Agents to Growing Fibroid Cell Populations

| Substrate Tested: | $IC_{50}$ (= 80 ng) Concentration: | $NG_0$ (= 32 ng) Concentration: |
|---|---|---|
| α-Tocopherol succinate | 22 μM | 38 μM |
| Troglitazone | 12 μM | 50 μM |
| Pioglitazone | 40 μM | 88 μM |
| Rosiglitazone | 40 μM | 90 μM |
| α-Tocopherol | 27 μM | N/A |
| β-Tocopherol | N/A | N/A |

$IC_{50}$ = (96 ng/well − $NG_0$)/2 + $NG_0$ = 64 ng/well
$NG_0$ = 32 ng/well

The $IC_{50}$ was the point on the graph where the increase in DNA content of the treated wells was 50% of the increase in DNA content of controls wells over the course of the experiment. The significance of the $IC_{50}$ point was that it represented an estimated point relative to which a substrate may in part be gauged as an effective FGI agent. The $NG_0$ (no net growth) was the point on the graph corresponding to the time=0 or starting DNA content of the wells. The significance of the $NG_0$ point was that any concentration of substrate that exhibited less DNA content per well than the $NG_0$ point had accomplished net reduction in the size of the leiomyoma cells population. N/A indicated that the listed condition was not attained in the experiment.

Conclusion: Some very unexpected results were obtained from this experiment. Generally, FIG. 3A shows that a dose dependent inhibition of fibroid leiomyoma cell proliferation occurred for each of the FGI agents assayed. However, two salient and unexpected results of the present invention are exhibited in FIG. 3A. The first was the early onset and intensity of the of anti-proliferative activity troglitazone. The second unexpected result was the substantial anti-proliferative activity of α-tocopherol succinate at physiologically equivalent concentrations. This substantial efficacy of α-tocopherol succinate for inhibiting fibroid leiomyoma cell proliferation was all the more unexpected in view of the markedly lower activity of α- and β-tocopherols in the same system. This result was all the more significant because it evidenced an ability of α-tocopherol succinate, a physiologically well tolerated substrate, to actually decrease the size of a population of uterine fibroid cells, and not merely decrease its rate of proliferation. In fact, the results of this experiment indicated that apoptosis, programed cell death, in populations of uterine fibroid cells was accomplished at physiologically or pharmacologically equivalent concentrations of either α-tocopherol succinate or troglitazone added to the milieu of the fibroid cell population.

Figure 3B:
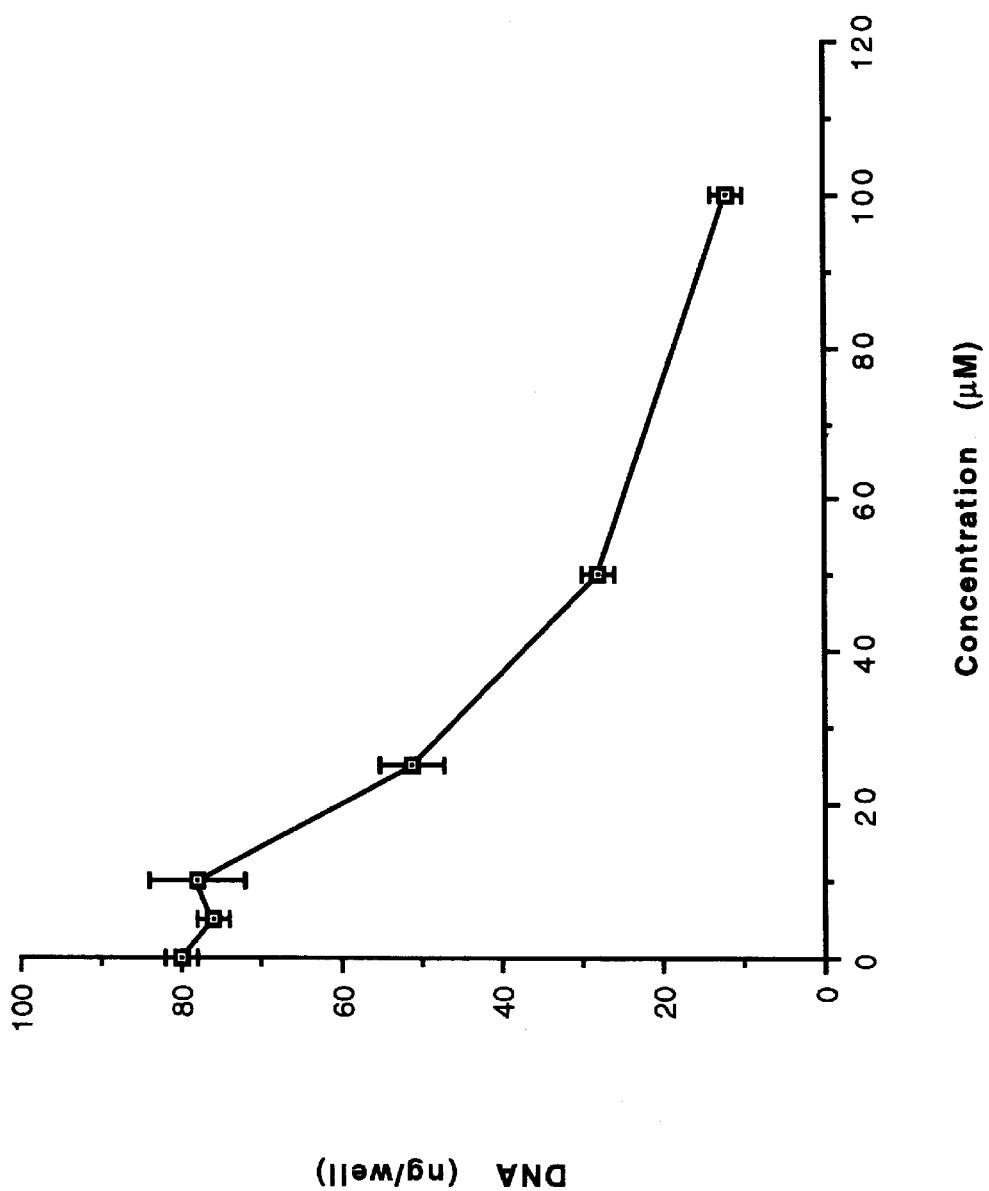
FIG. 3B is a dose response curve showing the effect of α-tocopherol succinate on the growth of cultured uterine fibroid leiomyoma cells.

FIG. 3B is a graph of the results for α-tocopherol succinate from a separate experiment under conditions similar to Example 1. Here, the DNA content of treated wells was determined at time=6 days. The area under the horizontal line indicates the concentration at which net cell death occurred in this experiment (~38 μM). This result again indicated that α-tocopherol succinate is a very potent FGI agent, that not only inhibited leiomyoma cell proliferation, but actually caused a net reduction in the size of the cell population. Further, these results were accomplished at physiological and near pharmacological serum equivalent concentrations in the experiment described.

In the experimental system of Example 1 (and Example 2 below), the background concentration of tocopherols was estimated as 10 μM. As shown in FIG. 3A, the experiment of Example 1 demonstrated that uterine fibroid cell populations continued to grow in the presence of this background concentration of tocopherols, as well as upon the addition of low levels of α- and β-tocopherols and α-tocopherol succinate. This can be seen more clearly in FIG. 4A. This result was expected, as fibroids were known to form and grow in humans in the presence of background tissue levels of α-tocopherol of about 3 μmoles per gram of wet tissue weight. Tissue levels of α-tocopherol were about the same in both normal uterine myometrium and in uterine leiomyomata. (Prabhudas et al., *Lipid-Soluble Antioxidants: β-Carotene and α-Tocopherol Levels in Breast and Gynecologic Cancers,* Gynecologic Oncology, 55:72–77 (1994)).

EXAMPLE 2

Growth of Leiomyoma Cells in the Presence of Background Levels of α-tocopherol and β-tocopherol Method: See Example 1 above generally. Vitamin C, an antioxidant that is not an identified potential FGI agent, was used as an experimental substrate control.

Figure 4A:
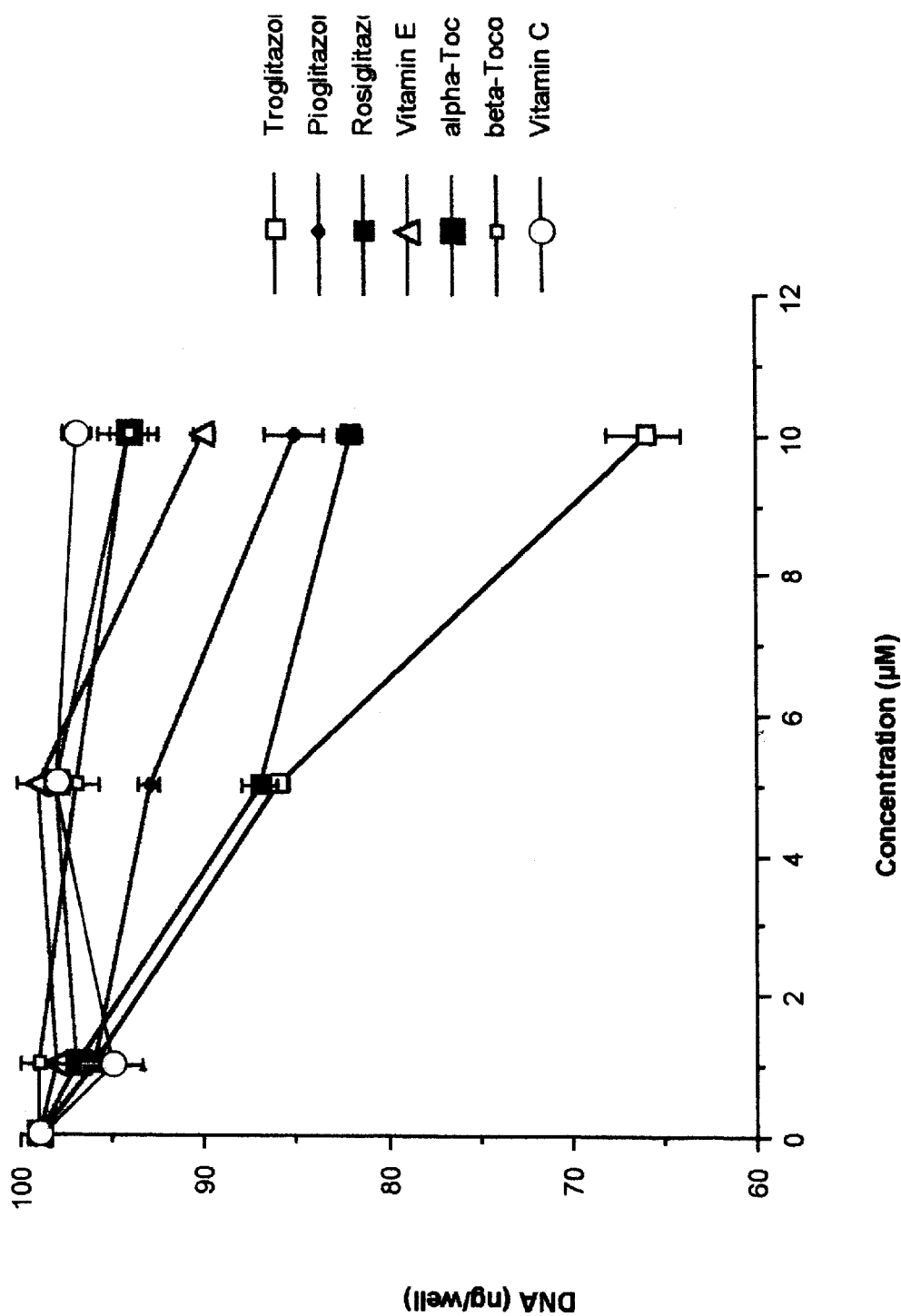
FIGS. 4A & 4B are graphic representations of the dose dependent inhibition of the growth of leiomyoma cells treated with different FGI agents in the experiment of Example 2.
Figure 4B:
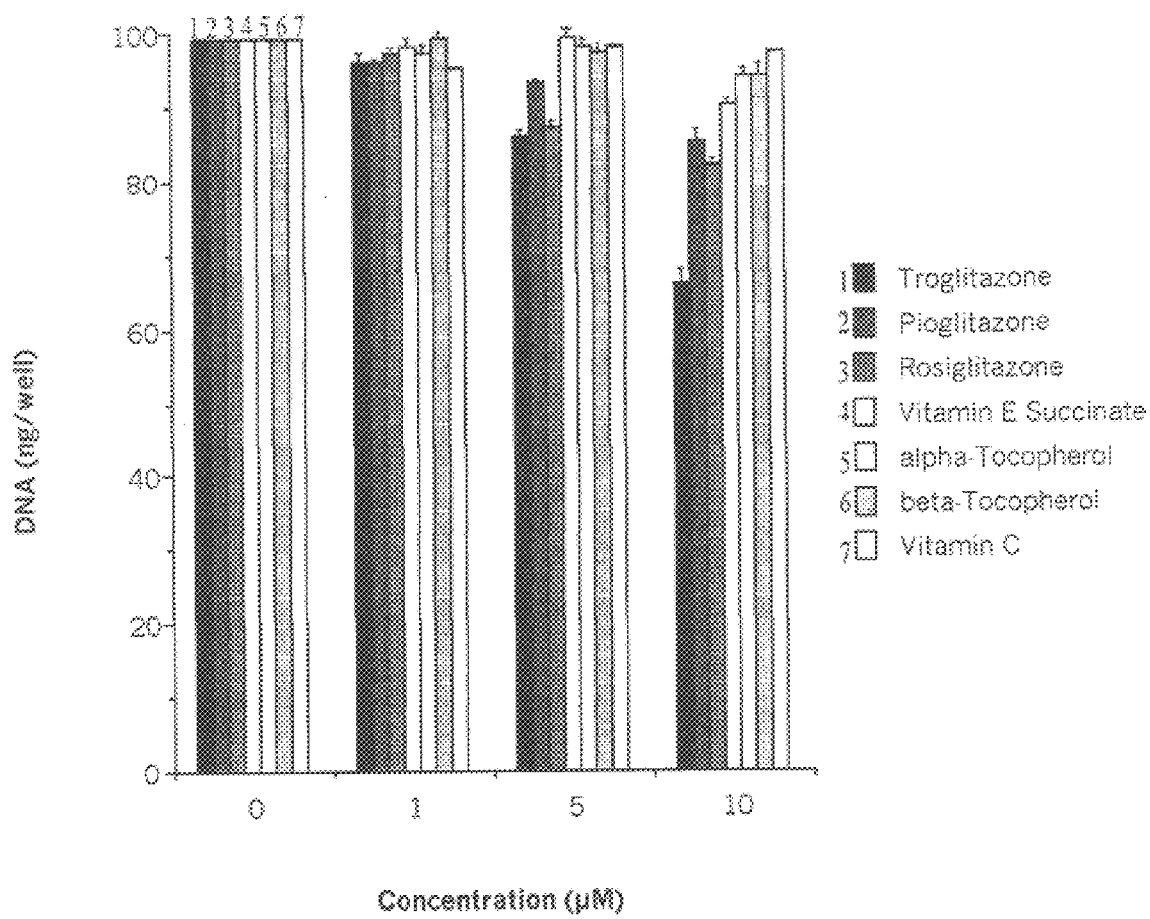

Results: The results are illustrated in FIGS. 4A and 4B. The DNA concentration of controls at time=4 days was 99+/−0.2 ng/well (the "0" concentration in FIGS. 4A & 4B). Growth of uterine fibroid cells clearly occurred in the presence of a background concentration of tocopherols. In fact, as shown in FIG. 4A, uterine fibroid cell populations continued to grow and increased in size substantially uninhibited in the presence of increased concentrations of added α- and β-tocopherols and α-tocopherol succinate ranging from 1 to 5 μM. However, upon the addition of 10 μM over back ground tocopherol treated wells began to show detectable inhibition of the growth of uterine fibroid cell populations.

Conclusion: As shown in FIGS. 4A & 4B, Vitamin E (α- and β-tocopherol) and the Vitamin E derivative, α-tocopherol succinate, exhibited little or no growth inhibition at lower concentrations. The absent or minimal effect of the addition of low concentrations over background of α- and β-tocopherols on fibroid cell proliferation shown in FIG. 4A was expected. In view of the presence of these substrates in normal uterine and in fibroid tissues, the continued fibroid cell population growth in the presence of low concentrations of α- and β-tocopherols mimicked the situation in humans. However, the more immediate effect on cell proliferation of some of the other FGI agent assayed was unexpected. Specifically, the immediate effect of troglitazone in low concentrations was very unexpected. The results of the experiment of Example 2 supported the results found in Example 1.

The experimental results shown in FIGS. 3A & 3B and FIGS. 4A & 4B give the concentrations of the various FGI agents tested at which inhibition of fibroid cell growth was detectable, and the concentrations at which an $IC_{50}$ was attained, if at all. For the non-tocopherol FGI agents tested in Example 2, inhibitive activity was detectable at the addition of substrate concentrations of only 1.0 μM above background, and inhibition clearly occurred at 5.0 μM. In the same experiment, for the tocopherol FGI agents tested, inhibitive activity was clearly detectable at the addition of substrate concentrations of 10.0 μM above background. Delivery of sufficient FGI agent into the milieu of any population of fibroid cells which results in a similar concentration of FGI agent in the milieu of the targeted cell population is expected to be similarly efficacious proliferation inhibitor as in Examples 1 and 2.

Figure 5A:
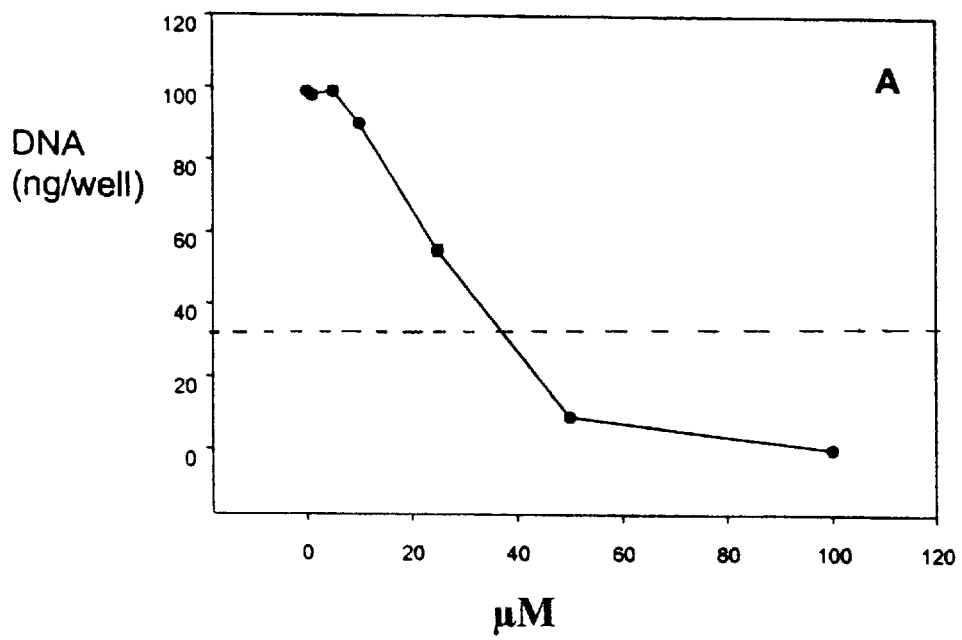
FIGS. 5A & 5B are graphs showing a comparison of the effect of a non-tocopherol related protein kinase C inhibitor (GF109203x) to that of α-tocopherol succinate on the growth of uterine fibroid leiomyoma cells.
Figure 5B:
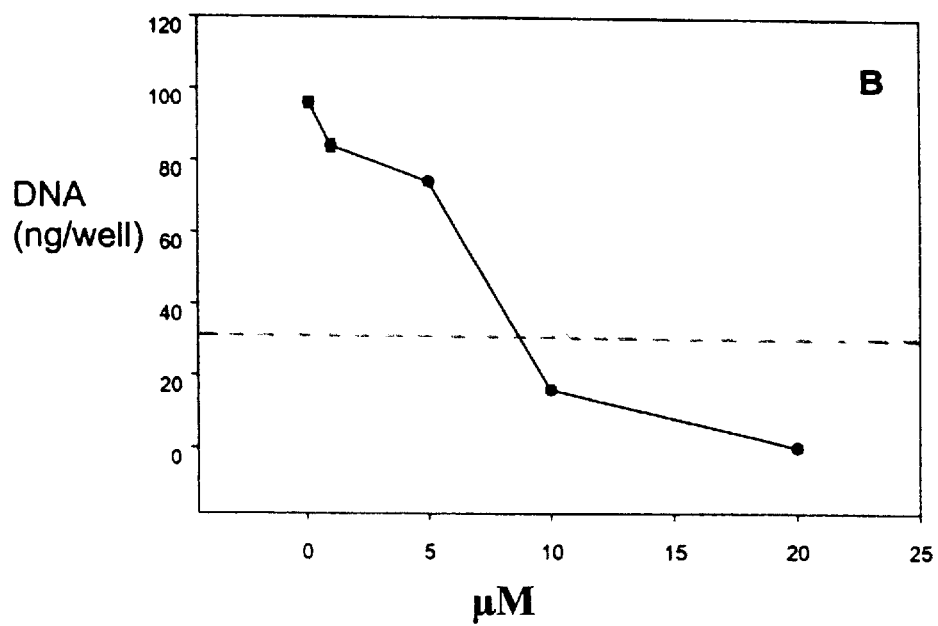

Clearly from Examples 1 & 2, tocopherol related substrates are potential FGI agents. This was expected because of tocopherol's effect on the PKC pathway. However, non-tocopherol related substrates that can appropriate appropriately effect the PKC pathway were also identified as potential FGI agents. Therefore, GF109203x, a protein kinase C inhibitor, was tested in an experiment similar to that of Example 1 to determine the efficacy of a non-tocopherol related, identified potential FGI agent to inhibit fibroid leiomyoma cell proliferation. Here, the DNA content of treated wells was determined at time=6 days. FIGS. 5A & 5B are graphs of the results of this experiment for α-tocopherol succinate (5A) and GF109203x (5B). A comparison of FIG. 5A with 5B shows that not only was the protein kinase C inhibitor (GF109203x) properly identified as a potential FGI agent, but it exhibited about a 5 time greater efficiency at inhibiting fibroid leiomyoma cell proliferation than α-tocopherol succinate in this experiment.

The results shown in Examples 1 & 2 support the determination of FGI agents in the practice of the present invention to include substrates that are α-tocopherol derivatives; α-tocopherol analogues, protein kinase C pathway inhibitors, protein kinase C inhibitors (e.g., thiazolidinediones; note: troglitazone is one of this class of compounds, and additionally is a tocopherol analogue or derivative in that its structure includes a tocopherol moiety), MAP kinase pathway inhibitors. The ordinary skilled artisan without undue experimentation in view of the teaching herein is able to identify and practice other FGI agents to accomplish the utility of the present invention.

In the preferred embodiment of the present invention, an FGI agent is administered non-systemically. This means that the FGI agent is not introduced intravenously or administered orally. Intra-vaginal delivery is a preferred means of accomplishing the non-systemic administration object of the present invention. The intra-vaginal delivery of FGI agents utilizes the "first uterine pass effect" as a substrate transport mechanism to preferentially deliver a vaginally administered substrate to the uterus. The first uterine pass effect delivering the FGI agent non-systemically to the uterine tissue generally and into the milieu of the fibroid cells to be inhibited. This is accomplished without first passing the substrate through the general circulation. Once the uterine fibroid cells are exposed to the FGI agent in sufficient concentration, the growth of the uterine fibroid cells is inhibited.

EXAMPLE 3

First Uterine Pass Effect

Preferential Vagina-to-uterus Substrate Transport Mechanism

The "first uterine pass effect" results in higher than expected substrate concentrations in uterine tissue after vaginal administration of an appropriate substrate.

Background: It is known that after vaginal administration of a drug that an unexpectedly high concentration of the drug appears in uterine tissue relative to the concentrations observed at the same time in the blood. The "first uterine pass effect" provides an explanation for this known observation.

The "first uterine pass effect" was defined as a targeted delivery system by Bulletti et al. (*Targeted drug delivery in gynaecology: the first uterine pass effect*, Human Reproduction, v12(5): 1073–1079 (1997), incorporated herein by reference). Bulletti et al. described and used the uterine first pass effect to preferentially transport to the uterine tissue, a vaginally administered, oil soluble substrate (progesterone). Five hours after administration, the substrate had diffused to the entire uterus and had reached steady state. Therefore, the ability to vaginally administer an oil soluble substrate in a lipid carrier, and preferentially transport the substrate to the uterus, and fully perfuse the uterine tissue with the substrate is known in the art.

Conclusion: According to Bulletti et al., for the uterine first past effect to be accomplished required only that the substrate, in a lipid-based carrier, be delivered into contact with the surface of the vagina proximate the cervix. Such delivery of the FGI agents of the present invention is readily accomplished. The tocopherols ($\alpha$-tocopherol, $\beta$-tocopherol and $\alpha$-tocopherol succinate) are directly oil soluble. The thiazolidinediones (troglitazone, rosiglitazone and pioglitazone) are soluble in organic solvent, and therefore, can be composed in a lipid based vehicle as well. Therefore, these FGI agents are well suited for transport to uterine tissue via the first uterine pass effect transport mechanism. They need only be delivered into contact with the surface of the vagina proximate the cervix. The preferred FGI agents of this group are $\alpha$-tocopherol, $\alpha$-tocopherol succinate and troglitazone.

EXAMPLE 4

Intra-vaginal Delivery of FGI Agents

Drug delivery methods, drug carrier compositions and drug delivery devices for the intra-vaginal delivery of drugs are known in the art and are commercially available by prescription and over the counter.

Intra-vaginal Delivery Methods: Vaginal drug delivery methods are well known in the art. A large variety of commercial and pharmaceutical products are available which vaginally deliver a therapeutic substrate.

Drug Carrier Compositions: In addition to known drug carrier compositions, absorption-enhancing agents are also known in the art for practice in vaginal drug delivery. See Alexander et al., U.S. Pat. No. 4,963,525.

Vaginal Drug Delivery Vehicles: These include suppositories, creams and gels, micro-capsules, and similar means. Vaginal drug delivery vehicles also include tampons, pessaries and intra-vaginal drug dispensing devices. These dispensing devices are available in a variety of configurations. Examples of such delivery vehicles include: INTRAUTERINE PROGESTASERT, a progesterone IUD; ESTRING, an intra-vaginal plastic ring for local estrogen release to the surrounding vagina and urinary tract; and CRINONE, vaginal progesterone gel for delivery to uterine endometrium in a polycarbophil base. Recent examples in the art of intra-vaginal drug dispensing or releasing devices include: Saleh et al., U.S. Pat. No. 5,072,372; Anderson et al., U.S. Pat. No. 5,816,248; and Nabchi, U.S. Pat. No. 5,788,980.

The intra-vaginal delivery method is preferably practiced by inserting a vehicle containing a composition of the present invention into the vagina of a subject to be treated for uterine fibroids, proximate the uterus, and in communication with a wall of the vagina. Then releasing composition containing an FGI agent from the composition into communication with the vaginal tissue of the vaginal wall and effecting the transport of the agent from the vaginal tissue to the uterine tissue via the first uterine pass mechanism and into communication with the milieu of the uterine fibroid to be treated.

When the composition is contained in a vaginal release device, the device is inserting into the vagina of a subject to be treated for uterine fibroids, proximate the uterus (cervix), and in communication with the wall of the vagina. The composition containing the agent is then dispensed or released from the device into communication with the tissue of the vaginal wall. Upon the composition coming into communication with the tissue of the vagina, the FGI agent is transported from the vaginal tissue to the tissues of the uterus and into the milieu of the uterine fibroid cell population via the first uterine pass mechanism.

The composition containing the FGI agent may be packaged in a vehicle that provides for the timed release of the FGI agent, or in a intra-vaginal delivery device that provides for the controlled release of the FGI agent.

EXAMPLE 5

In Situ Delivery of FGI Agents

Another preferred means of accomplishing the non-systemic administration object of the present invention is the in situ delivery method. The in situ delivery method involves the injection of a composition containing a FGI agent proximate or directly into the milieu of a fibroid cell population to be treated.

In Situ Delivery Methods: In practicing this method, a hypodermic needle or similar probe is inserted into or proximate the milieu of the target cell population. Insertion and positioning of the probe may be accomplished by any of a number of means known in the art. Deep tissue insertion of a needle or probe may be accomplished by direct puncture, or by making a pilot incision in the skin through which the probe is inserted. Guidance of the probe may be accomplished by palpation or the use of sonography, x-ray or other known guidance means. The preferred positioning of the probe depends in part on the size of the target cell mass and the effect desired to be accomplished. Once positioned, a composition containing the FGI agent can be passed through the bore of the probe and into communication with the milieu of the target cell population.

Drug Carrier Compositions: Consideration for practicing a carrier in a composition of in situ delivery is similarly resolved as for Example 4 above, by reference to the current art in the field and the normally skilled artisan, such as a formulary pharmacist.

In Situ Drug Delivery Vehicles: Compositions of the present invention for in situ delivery may be formulated in a vehicle that is a biocompatible liquid or gel which is injectable into or proximate the milieu of a uterine fibroid cell population. Alternatively, in a preferred embodiment, the compositions are formulated as micro- or nano-sized capsules or particles and suspended in an injectable vehicle. The formulation and injection of micro-particles is known in the art, and readily practicable by the ordinary skilled artisan. Recent examples of micro-particle methods of production and use include: Woiszwillo et al., U.S. Pat. No. 5,981,719; and Ragavan et al., U.S. Pat. No. 5,993,856.

Conclusion: The deep tissue injection of such time-release formulations for the delivery of reproductive system acting substrates, particularly in the form of different types of micro-capsules, is known and long practiced in the art. See Beck et al., Long-acting injectable microsphere formulation for parenteral administration of levonorgestrel, Advances in Contraception, 1:119–129 (1985), and Bhasin et al., *A Biodegradable Testosterone Microcapsule Formulation Provides Uniform Eugonadal Levels of Testosterone for 10–11 Weeks in Hypogonadal Men,* Journal of Clinical Endocrinology and Metabolism, 74(1):75–83 (1992). Therefore, the tissue injection of time-release micro-encapsulated substrates for affecting the reproductive system is known in the art, and practicable in the present invention by the ordinary skilled artisan.

The in situ delivery method has the capability of accomplishing delivery of a large dose of composition locally. In situ delivery of a FGI agent composition in an injectable liquid or gel may be utilized to acutely deliver a high concentration of FGI agent to quickly maximize inhibitory effects locally. Such delivery is useful when it is desired to directly treat a large localized uterine fibroid cell mass. However, the in situ delivery of an injectable vehicle containing the composition of the present invention as a suspension of time-release, or controlled release micro-particles is preferred for more long-term delivery of FGI agents. The micro-capsules or particles may be a combination of quick- or timed-release formulations as selectable by the ordinary skilled artisan, to accomplish a desired treatment regime. In practice, the micro-capsule vehicle is injected into the uterus of a subject to be treated proximate or into the fibroid cell population, causing the composition containing the agent to be released from the micro-capsules; and allowing the agent released from the micro-capsules to be communicated into the milieu of the uterine fibroid cells. The micro-particlized composition may be a combination of quick-release and time-release formulations of FGI agent, depending on the physical features (e.g., size) of the fibroid mass, and the projected time course of the treatment regime. Controlled or timed release of FGI agent can be accomplished by formulating the FGI agent in a time-release composition or vehicle.

While the above description contains many specifics, these should not be construed as limitations on the scope of the invention, but rather as exemplifications of one or another preferred embodiment thereof. Many other variation are possible, which would be obvious to one skilled in the art. Accordingly, the scope of the invention should be determined by the scope of the appended claims and their equivalents, and not just by the embodiments.

What is claimed is:

1. A non-systemic, non-invasive or minirally invasive method of treating uterine fibroids by inhibiting the growth of uterine fibroid cells comprising the steps of:

providing a dose of a composition, the composition including a fibroid cell growth inhibitor agent, the agent being a substrate or an analogue or derivative of a substrate that is normally present and physiologically well tolerated in humans and selected from the group consisting of: a tocopherol, a tocopherol derivative, a tocopherol analogue, a protein kinase C inhibitor, and a mitogen activated protein kinase inhibitor;

transporting the agent non-systemically into a milieu of the uterine fibroid cells to be inhibited; and exposing the uterine fibroid cells in the milieu to the agent to inhibit the growth of the uterine fibroid cells by increasing a background concentration of the agent in the milieu to a level sufficient to inhibit growth of the uterine fibroid cells.

2. The method of claim 1 wherein the providing step further comprises the fibroid cell growth inhibitor agent being selected from the group consisting of: a protein kinase C pathway inhibiting substrate and a mitogen activated kinase pathway inhibiting substrate.

3. The method of claim 2 wherein the fibroid cell growth inhibitor agent is a substrate selected from a class of compounds consisting of: a thiazolidinedione and a bisindolemalemide.

4. The method of claim 1 wherein the fibroid cell growth inhibitor agent is at least one substrate selected from the group consisting of: α-tocopherol, β-tocopherol, γ-tocopherol, α-tocopherol succinate, and troglitazone.

5. The method of claim 1 wherein the providing step further comprises the dose of composition includes the agent in an amount sufficient to sustain delivery of an effective amount of the agent to the uterine fibroid cells inhibit the growth of uterine fibroid cells after being transported into the milieu of the uterine fibroid cells.

6. The method of claim 1 wherein the providing step further comprises: providing a dose of a composition for intra-vaginal delivery of the composition to a subject to be treated for uterine fibroids.

7. The method of claim 1 wherein the providing step further comprises: providing a dose of a composition for in situ delivery of the composition to a subject to be treated for uterine fibroids.

8. The method of claim 6 wherein the providing step subsequently comprises:

inserting the composition into the vagina of a subject to be treated for uterine fibroids, proximate the uterus, and in communication with a wall of the vagina; and releasing the agent from the composition into communication with a vaginal tissue of the vagina wall for transport from the vaginal tissue to a uterine tissue via a first uterine pass mechanism.

9. The method of claim 1 wherein the transporting step further comprises: transporting the agent non-systemically into the milieu of the uterine fibroid cells to be inhibited via a first uterine pass mechanism.

10. The method of claim 7 wherein the providing step subsequently comprises:
   injecting the composition into a uterine tissue of a subject to be treated for uterine fibroids, proximate a population of uterine fibroid cells fibroid; and
   releasing the agent from the composition for transport into a milieu of the fibroid cells to be treated.

11. The method of claim 1 wherein the providing step further comprises: the dose being packaged in a vehicle for containing the composition and facilitating providing the composition.

12. The providing step of claim 11 wherein the dose is packaged in a vehicle selected from the group consisting of; suppositories, creams, gels, particle suspensions, biocompatable solutions, micro-capsules, tampons, pessaries, intra-vaginal dispensing devices and injectable media.

13. The method of claim 11 wherein the providing step subsequently comprises:
   inserting the vehicle into the vagina of a subject to be treated for uterine fibroids, proximate the uterus, and in communication with a wall of the vagina; and
   releasing the composition from the vehicle so that the agent comes into communication with a vaginal tissue of the vagina wall for transport from the vaginal tissue to a uterine tissue via a first uterine pass mechanism.

14. The method of claim 7 wherein the providing step subsequently comprises:
   injecting a vehicle containing the composition into a uterine tissue of a subject to be treated for uterine fibroids, proximate a population of uterine fibroid cells fibroid; and
   releasing the composition from the vehicle to allow transport of the agent into a milieu of the fibroid cells to be treated.

15. The method of claim 11 wherein the providing step further comprises: the dose being packaged in a controlled-release vehicle for containing the composition and releasing it in a controlled manner.

16. A system for inhibiting the proliferation of uterine fibroid leiomyoma cells comprising:
   a cell population of said leiomyoma cells in which the growth of said cells is to be inhibited;
   a fibroid cell growth inhibitor agent effective to inhibit the growth of said cells;
   a vehicle for containing and delivering said agent to a communication means; and
   a communication means for transporting said agent to said cells so that said agent can inhibit the proliferation of said uterine leiomyoma cells.

* * * * *